United States Patent [19]

Hing

[11] Patent Number: 5,249,327
[45] Date of Patent: Oct. 5, 1993

[54] STRING AND RIBBON FLOSS HOLDER FOR BRUSHES

[75] Inventor: Ally O. Hing, Superior, Ariz.

[73] Assignee: Marilyn O. Hing, Tucson, Ariz.

[21] Appl. No.: 935,570

[22] Filed: Aug. 26, 1992

[51] Int. Cl.$^5$ .............................................. A46B 9/06
[52] U.S. Cl. ....................... 15/104.94; 15/160;
        15/207.2; 15/DIG. 5; 15/DIG. 6; 132/120;
        132/308
[58] Field of Search ............... 15/104.94, 107, 110,
        15/114, 159.1, 160, 167.1, 186–188, 207.2,
        DIG. 5, DIG. 6; 132/120, 308, 309, 313, 323

[56]                References Cited

U.S. PATENT DOCUMENTS

| | | | |
|---|---|---|---|
| 205,349 | 6/1878 | Butron | 132/120 |
| 1,569,165 | 1/1926 | Wolf | 15/167.1 |
| 1,673,638 | 6/1928 | Peterson | 15/104.94 |
| 1,725,852 | 8/1929 | Cressler | 15/104.94 |
| 2,267,498 | 12/1941 | Foliot | 15/160 |
| 2,702,914 | 3/1955 | Kittle et al. | 15/114 |
| 3,103,679 | 9/1963 | Clemens | 15/167.1 |
| 3,295,156 | 1/1967 | Brant | 15/167.1 |
| 3,668,732 | 6/1972 | Lardenois | 15/207.2 |
| 4,014,064 | 3/1977 | Okazahi | 15/207.2 |
| 4,030,845 | 6/1977 | Deckert | 132/308 |
| 4,277,297 | 7/1981 | Thornton | 156/161.1 |
| 4,616,374 | 10/1986 | Novogrodsky | 15/167.1 |
| 4,724,569 | 2/1988 | Eguchi et al. | 15/DIG. 5 |
| 4,811,445 | 3/1989 | Lagieski et al. | 15/104.94 |
| 5,063,948 | 11/1991 | Lloyd | 132/321 |
| 5,074,005 | 12/1991 | Mach | 15/105 |

FOREIGN PATENT DOCUMENTS

| | | | |
|---|---|---|---|
| 1938937 | 2/1971 | Fed. Rep. of Germany | 15/186 |
| 3528596 | 2/1987 | Fed. Rep. of Germany | 15/167.1 |
| 668611 | 7/1929 | France | 15/207.2 |
| 582351 | 9/1958 | Italy | 15/114 |
| 479277 | 10/1969 | Switzerland | 15/207.2 |
| 363270 | 12/1931 | United Kingdom | 15/167.1 |

Primary Examiner—Harvey G. Wornsby
Assistant Examiner—Mark Spisich
Attorney, Agent, or Firm—Warren F. B. Lindsley

[57]                ABSTRACT

A brush having a plurality of tufts extending outwardly thereof in a common direction and having a floss holder in one or more of the tufts through which extends a string or web of a floss material and outwardly of the bristles for hand or machine held cleaning and enhancing purposes.

3 Claims, 3 Drawing Sheets

U.S. Patent  Oct. 5, 1993  Sheet 1 of 3  5,249,327
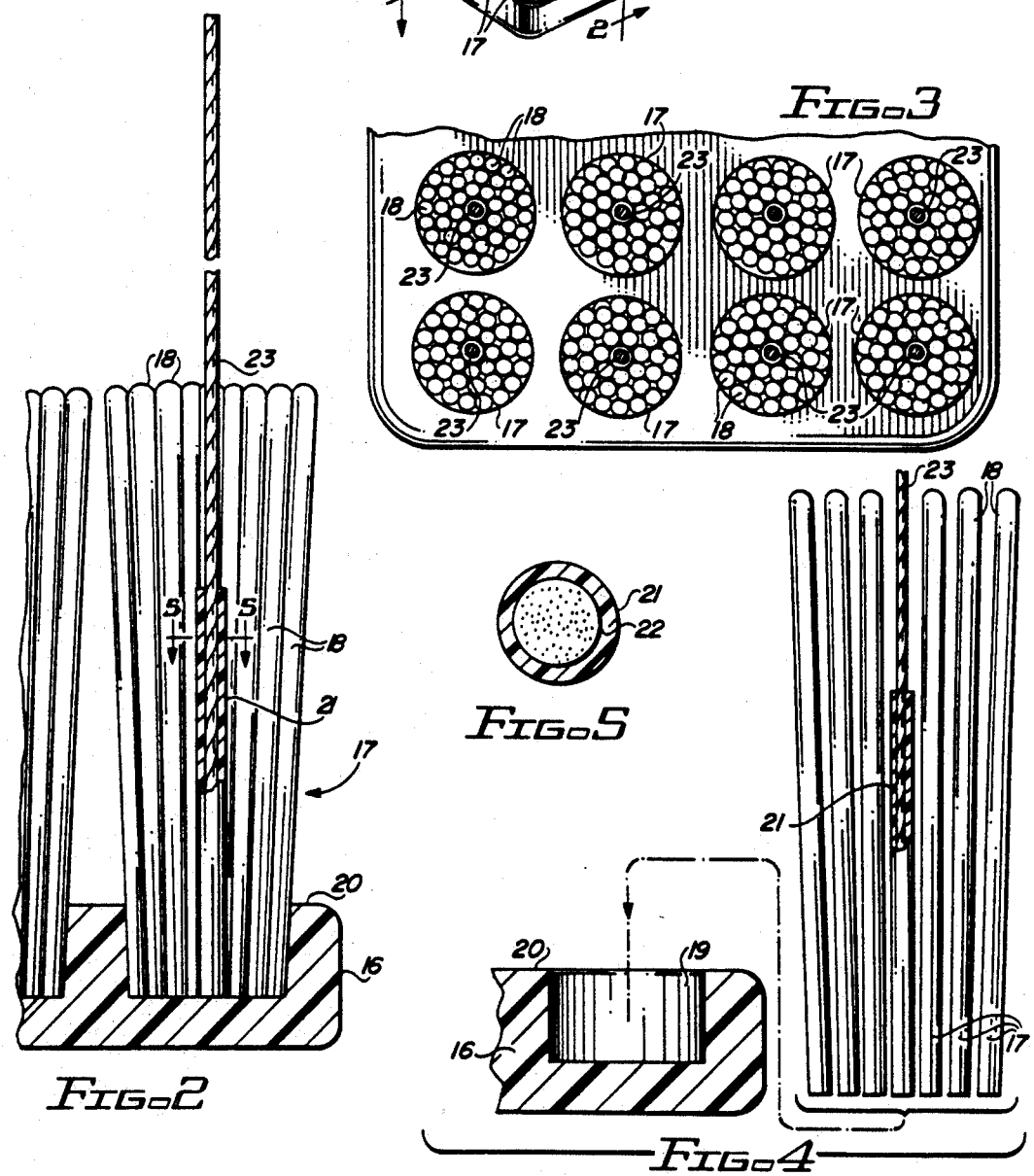

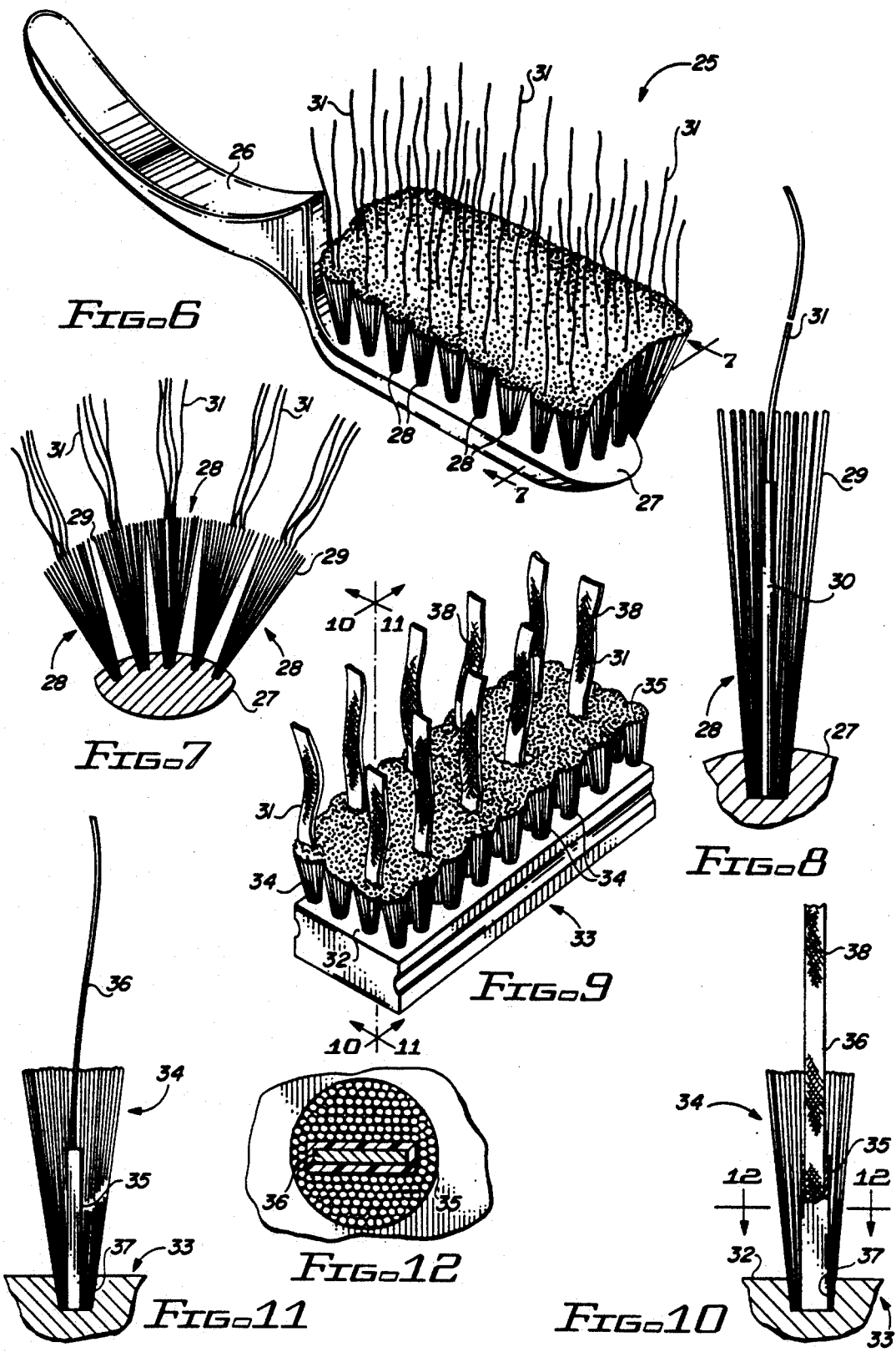

STRING AND RIBBON FLOSS HOLDER FOR BRUSHES

BACKGROUND OF THE INVENTION

This invention relates to brushes and more particularly to handpieces combining dental floss with the bristles of a brush such as toothbrushes, scrub brushes and the like.

Over the years, many different types of brushes have been designed with some brushes dispensing paste or other viscous substances into the region of the bristles from a container which may form the handle of the brush.

While it is known to provide toothbrushes having cleaning material containing handles for dispensing solutions to the region of the bristles of the brush, such prior art designs have not disclosed a bristle and floss brush combination providing dual purpose cleaning functions.

DESCRIPTION OF THE PRIOR ART

U.S. Pat. No. 4,616,374 discloses a toothbrush in which interlaced loops are combined with conventional bristles.

U.S. Pat. No. 5,074,005 discloses a toothbrush having a floss bundle cleaning element instead of conventional bristles.

U.S. Pat. No. 3,295,156 discloses a toothbrush having normal and flagged bristles.

U.S. Pat. No. 3,103,679 discloses a toothbrush having shorter larger diameter bristles along with smaller diameter longer bristles.

Other patents of interest comprise U.S. Pat. Nos. 4,227,297 and 5,063,948.

None of these prior art patents individually or in combination disclose the claimed brushes having floss projecting from the bristles of the tufts for dual purpose cleaning functions in the manner disclosed.

SUMMARY OF THE INVENTION

In accordance with the invention claimed, a new and improved dual purpose brush is disclosed for combined bristle and floss cleaning functions.

It is, therefore, one object of this invention to provide a new and environmentally improved brush having a dual purpose head for brushing and flossing action wherein the floss is joined with one or more tufts of the bristles in the brush head.

Another object of this invention is to provide a new and improved brush head, the head of which comprises a plurality of floss strands or webs extending outwardly of the bristles.

A further object of this invention is to provide a new and improved combined toothbrush and floss holder wherein a string or web of floss is contained with each tuft of bristles and extending outwardly therefrom for teeth flossing purposes.

A still further object of this invention is to provide a new and improved brush wherein one or more tufts of the brush are provided with a floss holder extending axially thereof a distance shorter than the length of the bristles of the tuft and containing floss extending outwardly and beyond the end of the bristles of the tuft for cleaning purposes.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWINGS

The present invention may be more readily described by reference to the accompanying drawings wherein:

FIG. 1 is a partial perspective view of one embodiment of this invention illustrating a toothbrush head having a strand of floss extending outwardly thereof from each tuft of bristles;

FIG. 2 is a cross sectional view of FIG. 1 taken along the line 2—2;

FIG. 3 is a cross sectional view of FIG. 1 taken along the line 3—3;

FIG. 4 is an exploded view illustrating how a tuft of bristles is inserted into an opening in the head of a toothbrush;

FIG. 5 is a cross sectional view of FIG. 2 taken along the line 5—5;

FIG. 6 is a perspective view of a modification of the brush shown in FIG. 1 and embodying the invention;

FIG. 7 is a cross sectional view of FIG. 6 taken along the line 7—7;

FIG. 8 is a cross sectional view of one of the tufts shown in FIG. 7;

FIG. 9 is a further modification of the brushes shown in FIGS. 1 and 6 wherein the floss comprises a web of material;

FIG. 10 is a cross sectional configuration of FIG. 9 taken along the line 10—10;

FIG. 11 is a cross sectional view of FIG. 9 taken along the line 11—11;

FIG. 12 is a cross sectional view of FIG. 10 taken along the line 12—12;

DESCRIPTION OF THE PREFERRED EMBODIMENT

Figure 13:
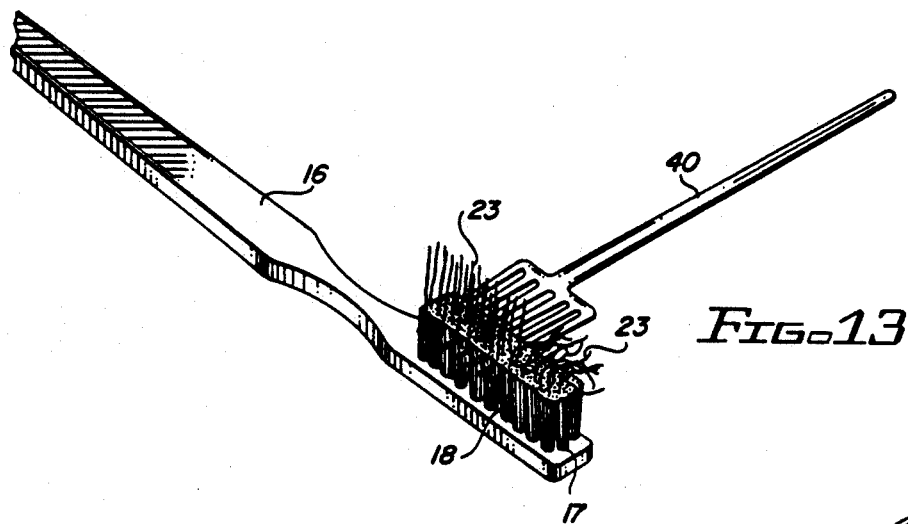
FIG. 13 is a perspective view of a toothbrush embodying the invention and illustrating a comb for lifting the floss out of the bristles after a brushing operation.

Referring more particularly to the drawings by characters of reference, FIGS. 1-3 and 5 disclose a toothbrush 15 comprising a handle 16 of any suitable material having tufts 17 of bristles 18 secured thereto at one end thereof for forming a brush for cleaning teeth. The brush end or head of the toothbrush has the overall appearance and proportions of any usual toothbrush head with its outermost end flattened for carrying tufts 17 of bristles 18. The arrangement and mode of bristle attachment can vary widely and in practice such bristles are installed in rows of tufts, as shown in FIGS. 1 and 3, with each tuft being carried in, suitably secured and projecting from an opening 19 in the face 20 of the flattened portion of the toothbrush. As shown in FIGS. 1 and 3, four rows of bristle tufts are shown although any number of rows and display arrangements may be used and still fall within the scope of this invention.

In accordance with the invention claimed, a string, cord or web of floss is intermixed with the bristles of the brush and arranged to extend outwardly thereof for tooth flossing or brush surface cleaning and polishing purposes.

As shown in FIGS. 1-5, the usual bristles of a toothbrush are inserted in prearranged apertures or holes in one end of the toothbrush and secured therein in any suitable known manner.

Inserted in approximately the center of each tuft 17 of bristles, 18 in a floss holder 21 one end of which is secured with bristles 18 of one or more tufts of the toothbrush in openings 19 in face 20 of handle 16. This hollow cylindrical member or holder 21 may be formed of a suitable pliable plastic or rubber like material 22 which bends in unison with the bristle in a tooth or teeth cleaning brushing action.

Extending through and outwardly of each of holder 21 is a strand or web of dental floss 23. Floss 23 and its holder 21 may be secured to the bottom of opening 19 in handle 16 as a part of tuft 17 or along a part or all of the inner surface of holder 21. As noted from FIG. 2, holder 21 extends only partially through the longitudinal length of tuft 17 of bristles 18 with floss 23 extending outwardly of the holder and the end of bristles 18 a predetermined distance.

This predetermined distance should be at least preferably greater than the length of bristles 18.

FIGS. 6-8 disclose a novel hand brush 25 for cleaning purposes comprising a handle 26 having a brush head 27 attached at one end thereto. The brush head has a plurality of tufts 28 secured in the upper surface thereof extending laterally therefrom. Each tuft comprises a plurality of bristles 29 having a floss holder 30 mounted therewithin and extending from the head of the brush coaxially with the bristles to their free ends and beyond a predetermined distance.

Each floss holder is provided with a strand of floss 31 mounted within and extending longitudinally thereof. As shown in FIGS. 6-8, a portion of the floss extends outwardly of the free ends of bristles 29 a distance at least as great as the length of the bristles.

It should be noted that this invention is environmentally sensitive, since hair enhancing-treating ingredients may be added directly to the floss of the brush in an even manner thereby aiding in eliminating the use of an aerosol hair spray and its FREON content.

FIGS. 9-12 disclose a further modification of the brushes shown in FIGS. 1-8 wherein face 32 of a brush 33 is provided with a plurality of tufts 34 formed from a grouping of bristles 35 spacedly arranged to extend outwardly of face 32 in the same manner as described for the bristles of the brushes shown in FIGS. 1-8.

One or more of the tufts are provided with a holder 35 through which extends a web of floss or other strip like material 36. The holders are mounted in suitable openings 37 in face 32 of brush 33 and arranged to extend through tubes or holders 35 and outwardly of the free ends of the bristles of the brush as shown in FIGS. 9-12.

The strip of material 36 may be impregnated with or contain a surface of a suitable cleaning or polishing material 38 that becomes functional when the strips of material 36 are bent and lie flat on the surface being rubbed by the brush.

If desired, material 36 may be impregnated with or contain a surface having hair treatment material thereof which is rubbed off on to the hair or scalp when the brush is used thereon.

FIG. 13 illustrates a comb 40 for use in repositioning floss 23 when it becomes matted with bristles 18 of the brush.

Figure 14:
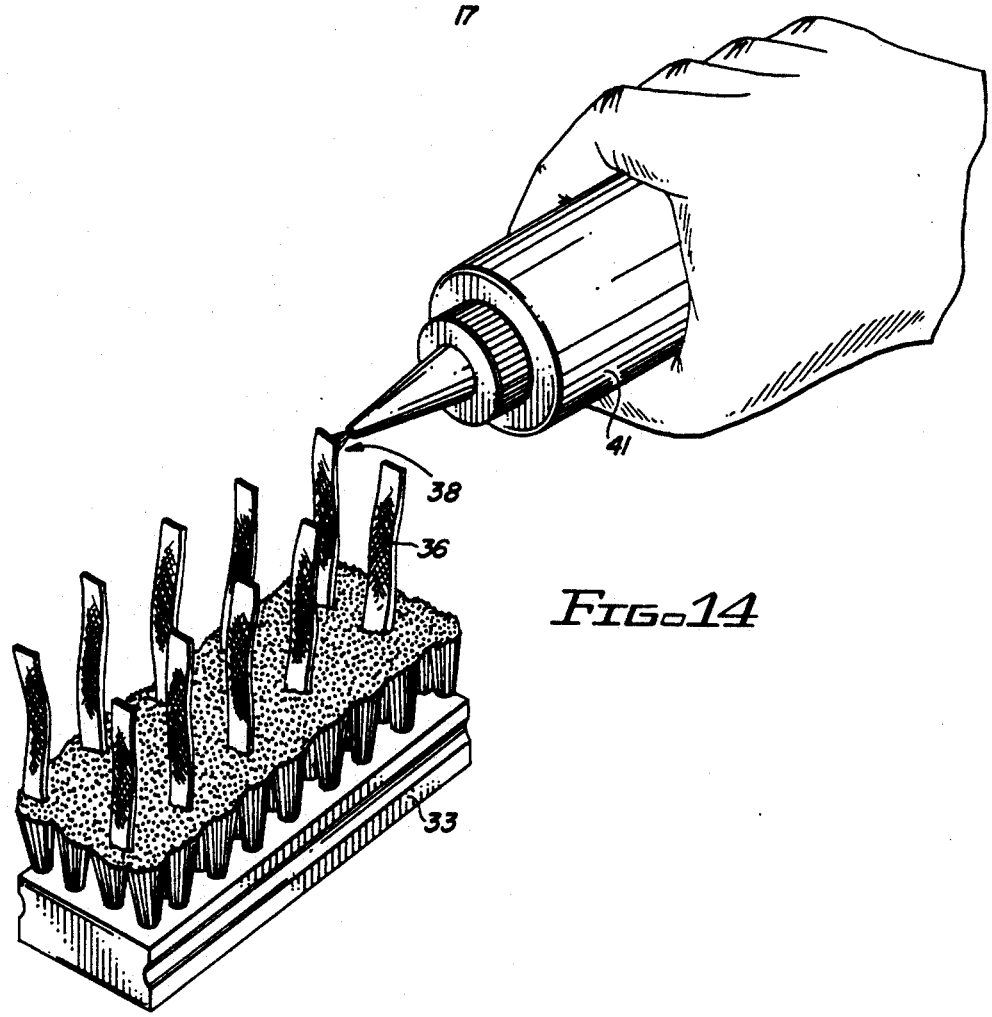
FIG. 14 is a perspective view of a brush illustrating the application of oil, hair enhancer and/or cleaning fluids or pastes to the floss of the brush.

FIG. 14 illustrates a resilient push bottle 41 for applying material 38 to the strip material 36 of brush 33.

Although but a few embodiments have been illustrated and described, it will be apparent to those skilled in the art that various changes and modifications may be made therein without departing from the spirit of the invention or from the scope of the appended claims.

What is claimed is:

1. A hand held brush comprising:
a handle section and a brush section,
said brush section includes a flat surface having a plurality of spaced tufts extending outwardly of said flat surface in a common direction,
each of said tufts comprising a plurality of bristles substantially of the same length gathered at one end and secured at said one end to said flat surface,
a plurality of elongated elements extending outwardly of the other end of of said tufts in said common direction for cleaning purposes, and
each of said elements being mounted in a holder,
said holder comprising a hollow resilient tube mounted within and extending outwardly of said tufts a distance less than the length of said bristles.

2. The hand held brush set forth in claim 1 wherein:
said holder has a length at least half the length of said bristles.

3. The hand held brush set forth in claim 1 wherein:
said elongated elements comprise cleaning material disposed on it along its length.

* * * * *